United States Patent [19]

Cooke et al.

[11] Patent Number: 5,336,699
[45] Date of Patent: Aug. 9, 1994

[54] BONE CEMENT HAVING CHEMICALLY JOINED REINFORCING FILLERS

[75] Inventors: Francis W. Cooke, Wichita, Kans.; Thomas R. Marrero; Hirotsuga K. Yasuda, both of Columbia,, Mo.

[73] Assignee: Orthopaedic Research Institute, Wichita, Kans.

[21] Appl. No.: 998,881

[22] Filed: Dec. 28, 1992

Related U.S. Application Data

[63] Continuation of Ser. No. 838,317, Feb. 20, 1992, abandoned.

[51] Int. Cl.$^5$ ............................................. A61F 2/00
[52] U.S. Cl. ..................................... 523/115; 606/76; 523/116
[58] Field of Search ............... 523/115, 209, 212, 213, 523/222, 116; 606/76, 92

[56] References Cited

U.S. PATENT DOCUMENTS

| | | | |
|---|---|---|---|
| 4,587,278 | 5/1986 | Dotzauer | 523/222 |
| 4,727,096 | 2/1988 | Choudin | 523/222 |
| 4,822,826 | 4/1989 | Pommier et al. | 523/222 |
| 4,968,560 | 11/1990 | Lechner et al. | 523/213 |
| 4,970,261 | 11/1990 | Yu et al. | 523/222 |
| 4,990,549 | 2/1991 | Delvin et al. | 523/209 |
| 5,013,771 | 5/1991 | Guillet et al. | 523/213 |

OTHER PUBLICATIONS

Bever, Acrylics as Biomedical Materials; Adhesion: Fundamental Principles; Encyclopedia of Materials Science and Engineering; 1986.
Cooke, et al.; Strength and Structure of a C-Fiber Reinforced Commercial PMMA Bone Cement; Trans. Soc. for Biomaterials Meeting, 1981.
Wagner, et al.; Use of High-Performance Polyethylene Fibres as a Reinforcing Phase in Poly(methylmethacrylate) Bone Cement; Biomaterials, 1989, vol. 10, pp. 139–141.
Andreopoulos, et al.; Surface Treated Polyethylene Fibres as Reinforcement for Acrylic Resins; Biomaterials, 1991, vol. 12, Jan., pp. 83–87.
Fourdeyhimi, et al.; Elastic and Ultimate Properties of Acrylic Bone Cement Reinforced with Ultra–High–-Molecular–Weight Polyethylene Fibres; J. Biomed. Mat. Res., vol. 23, 63–80 (1989).
Wright, et al.; Mechanical Properties of Aramid Fiber Reinforced Acrylic Bone Cement; J. Materials, Sci., vol. 14, 1979, pp. 503–505.
Saha, et al.; Mechanical Properties of Bone Cement: A Review; J. Bio. Mat. Res., vol. 18 435–462 (1984).
Budinski, et al.; Engineering Materials Properties and Selection; Second Edition, 1983.
Reinhart, et al.; Engineered Materials Handbook, vol. 1, Composites, 1987; Pigliacampi, et al.; Organic Fibers.
Kusy, Characterization of Self–Curing Acrylic Bone Cements; J. Biomed. Mat. Res., vol. 12, 271–305 (1978).
Modacrylic Fiber Producers, 1987, pp. 355, 377–379 and 276.

*Primary Examiner*—Paul R. Michl
*Assistant Examiner*—LaVonda DeWitt
*Attorney, Agent, or Firm*—Hovey, Williams, Timmons & Collins

[57] ABSTRACT

Improved polymeric orthopaedic compositions are disclosed wherein sized, functional fibers are incorporated into a physiologically acceptable matrix. The compositions of the invention can be fabricated in the form of particulate powders adapted for reinforcment of bone cements, continuous media for such cements, and orthopaedic implant coatings. A complete implant attachment system is also provided, made up of a fiber reinforced implant coating, and a compatible fiber-reinforced cement. In preferred forms, the fibers have a layer of sizing thereover which is chemically joined both to the surface of the fibers and to the surrounding matrix, and the fibers are present at a level of at least about 6 volume percent. If desired, sized radiopaque particles may be incorporated into the compositions of the invention. The fibers are advantageously polymeric in nature and of intermediate stiffness, whereas the matrix fraction is preferably polymethylmethacrylate.

83 Claims, 1 Drawing Sheet

BONE CEMENT HAVING CHEMICALLY JOINED REINFORCING FILLERS

This application is a continuation of application Ser. No. 07/838,317, filed Feb. 20, 1992, now abandoned.

BACKGROUND OF THE INVENTION

1. Field of the Invention

This invention relates to improved polymeric orthopaedic compositions such as particulate powders, continuous media for bone cements, finished bone cements and orthopaedic implant coatings which are characterized by an amount of physiologically acceptable polymeric matrix with sized fibers dispersed in the matrix such that the sizing layer on the fibers is chemically joined to the surface of the fibers and to the matrix material. In preferred forms, sized radiopaque particles can also be added to the orthopaedic compositions.

2. Description of the Prior Art

Starting in the mid-1930s and continuing through the middle part of the 1950s, the orthopaedic implantation of artificial femoral heads, i.e., the ball of the hip joint, was achieved primarily by impaction of the stem of the implant into the medullary (marrow) cavity of the femur. Although this procedure achieved some degree of success in that it increased the mobility of certain patients suffering from hip joint deterioration or malfunction, the procedure had many shortcomings. The principal problem encountered was traced to loosening of the implant in a relatively few years, thus compromising the patient's mobility and oftentimes causing significant pain.

In the late 1950s, Dr. John Charnley in England proposed use of a mortar or grouting agent for cementing an orthopaedic appliance to a patient's bone structure using polymethylmethacrylate (PMMA) as the grout agent. The PMMA mortar material served to fill all of the spaces between the stem of the implant and the surrounding bone. In particular, it was determined that the PMMA grouting agent could be forced into the tiny interstices of the porous bone. This resulted in a mechanical lock of the grout agent to the bone. Another advantage of the PMMA system was the fact that mobilization of the patient following implantation could be accomplished at an earlier date following surgery, and the functional lifetime of the implant was greatly enhanced.

The success obtained in hip surgery using PMMA encouraged orthopaedic surgeons to develop implant attachment techniques for other prostheses such as the acetabular or cup side of the hip joint and for the femoral, tibial and patella components of total knee replacements. Although the life time of these prostheses has markedly improved and the range of patients for which the surgery is deemed appropriate has greatly increased, difficulties still remain. There is still a tendency for the cement mantle which surrounds the prosthesis to fail by brittle fracture and fatigue and, thereby, to lose its ability to transmit load from the implant to the bone structure. This loss of load transfer capability in turn was found to cause loosening of the prosthesis with concomitant joint dysfunction, failure of the metal prosthesis itself by virtue of loss of support, and finally pain during patient activity because of gross movement of the prosthesis.

Efforts to remedy these problems have not met with a great deal of success. One attempt involved increasing the thickness of the cement mantle. Another proposal chose to proceed in the opposite direction by significantly decreasing the thickness of the mantle. Thorough cleaning and lavage of the bony surfaces in order to promote interdigitation and better mechanical locking of the cement with the interstices of the bone structure was also tried. Other researchers suggested pressurization of the cement during insertion to further promote introduction of the cement into the interstitial spaces of the bone. Grouting guns were used to eliminate seams and laps in the cement mantle. Finally, incorporation of strong reinforcement fibers in the cement was tried, including 316 type stainless steel wires, cobalt-chromiummolybdenum implant alloy wires, glass fibers, aramid fibers and polyethylene terephthalate (PET). These prior procedures did not adequately solve the problem for two basic reasons. First, prior researchers failed to appreciate that although cement reinforcement was desirables their reinforcements (except PET) were so rigid and stiff that they actually bridged bone interstices impeding full filling of the interstitial cavities. Secondly, these same researchers made no attempt to chemically couple the fibers to the matrix polymer. Consequently, little or load was transferred to the fibers and they were unable to participate in load bearing. Accordingly, the fibers conferred little improvement in strength or crack resistance to the cement.

An exemplary effort in this respect was the attempt in the early 1980s to reinforce bone cement materials with carbon fibers. The fibers were added the powder mix so that upon consolidation of the bone cement, the fibers were only dispersed in the matrix phase but not in the original PMMA particles. Carbon fiber addition had little, if any, beneficial effect on the toughness of the bone cement because the fibers were not coupled to the matrix. Further, these very stiff fibers greatly impeded the intrusion of the cement into the small bony interstices. This product has subsequently been removed from the market.

SUMMARY OF THE INVENTION

The shortcomings of prior orthopaedic compositions and cements have now been overcome by the present invention wherein sized fibers designed to enhance the functional properties of orthopaedic compositions are incorporated into and chemically joined with a polymeric matrix. The principles of the invention can be employed in the fabrication of particulate powders adapted for use in bone cements, continuous media for such cements, and in coatings for orthopaedic implants.

In preferred forms, the fibers have a layer of sizing thereover which are chemically joined to the surface of the fibers, and also to the surrounding matrix. The fibers are broadly present in such orthopaedic comositions at a level of at lest 6 voluem percent, and have an average length of from about 1 $\mu$m to about 2 cm. Preferred fibers are selected fromt eh group consistign of polyaramids, polyesters, polyalkenes and polyamids. The matrix phase is advantageously selected from teh group consisting of a substituted or unsubstituted acrylate, most particularly polymethylmethacrylate. A variety of sizing agents can be employed, particularly those from the group consisting of ethyl silane, methylmethacrylate, ethylmethacrylate, ethylene, propylene and methane.

In preparing a particulate powder in accordance with the invention, the fibers are initially sized with MMA using glow discharge polymerization, whereupon the fibers are dispersed in liquid MMA monomer subjected to addition polymerization. The resulting bulk material is then reduced to a powder.

Fabrication of a bone cement involves placing the previously prepared powder in MMA monomer also having a quantity of previously sized reinforcing fibers therein, followed by polymerization of the monomer. This creates a continuous polymeric medium with the fiber-reinforced powder particles dispersed therein.

The fabrication of implant coatings is similar, except that such coatings generally do not contain the particulate powder fraction. Rather, these coatings comprise a continuous polymeric phase (e.g., PMMA) having previously sized reinforcing fibers therein. The coatings are adapted for application and chemical joinder to the outer surface of a rigid implant, in such fashion that the reinforcing fibers thereof extend outwardly from the coating surface.

A complete implant installation system is made up of a previously coated implant together with a bone cement. In practice, a precoated orthopaedic implant is inserted into a previously reamed and cement-filled bone cavity. The sized fibers reinforcing both the continuous media and the cement and the continuous phase of the coating, and the fibers protruding from the reinforcing cement particles, extend across the coating/bone cement interface to enhance the bonding and chemical joinder between the coating and cement. The implant is thus firmly held in place.

DETAILED DESCRIPTION OF THE PREFERRED EMBODIMENTS

Figure 1:
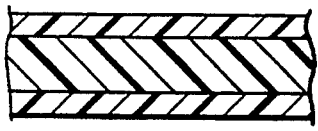
FIG. 1 is a schematic, greatly enlarged cross-sectional view of a part of a sized fiber forming a part of a reinforced orthopaedic composition.

A key principle of the present invention resides in the provision of a multiple-use orthopaedic composition broadly including an amount of a physiologically acceptable polymeric matrix material with a quantity of sized fibers dispersed in the matrix material. Such an orthopaedic composition can be fabricated as a particulate powder adapted for placement in a continuous medium to form a bone cement; as a continuous fluid medium useful in a bone cement context; or as a coating for application to an orthopaedic appliance.

In general, the orthopaedic compositions of the invention include fibers having a layer of sizing material thereover which is chemically joined to the surface of the fibers, with the sizing material on the fibers also being chemically joined to the matrix. Generally, the fibers are present in the orthopaedic compositions at a level of at least about 6 volume percent and have an average length of from about 1 $\mu$m to about 2 cm. The sizing material may be directly joined to the fibers, or use can be made of a coupling agent different from the matrix, such as a silane. The fibers are advantageously polymeric and are formed of a relatively high strength polymer of intermediate stiffness.

PARTICULATE POWDER

In one specific aspect of the invention, the orthopaedic compositions may be fabricated as powders especially adapted for use in bone cements. In such a context, the particles of the powder would have an average size of from about 5 to 100 $\mu$m, and are broadly made up of the polymeric matrix and sized fibers. Advantageously the fibers are of polymeric character and are selected from the group consisting of aramids, polyesters, polyalkenes and polyamids. The fibers should have a diameter of from about 1 $\mu$m to 100 $\mu$m, and more preferably at least certain of the fibers should have a diameter of from about 2-15 $\mu$m. The length of the fibers Is variable, depending upon desired end use.

Particularly good results have been found by using fibers having a stiffness (defined as the product of the tensile elastic modulus of the fibers and the area moment of inertia of the fibers) of from about $1.0 \times 10^{-13}$ to $150 \times 10^{-13}$ Nm$^2$, and more preferably from about $10 \times 10^{-13}$ to $75 \times 10^{-13}$ Nm$^2$. The room temperature fatigue strength of the fibers should be at least about 7 NPa at $10^6$ cycles, more preferably at least about 30 NPa at $10^6$ cycles.

In the specific context of particulate powders, the fibers should be present at a level of from about 6–70 volume percent, most preferably about 50 volume percent.

The matrix component is advantageously a substituted or unsubstituted acrylate, especially polymethylmethacrylate having a viscosity average molecular weight of not less than about $1 \times 10^5$ g./mole.

As indicated, the fibers forming a component of the particles should be sized. The sizing agent is normally selected from the group consisting of ethyl silane, methylmethacrylate, ethylmethacrylate, ethylene, propylene and methane. The most preferred sizing agents are the acrylates, specifically methylmethacrylate.

If desired, a radiopaque agent may be added to the particulate powder, and in such a case the radiopaque agent would have sizing material chemically joined thereto. The preferred radiopaque agent is zirconium dioxide, present at a level between 1-15% by weight of the powder. Barium sulfate is also acceptable. The radiopaque powder desirably has a diameter of about 1 $\mu$m, although other sizes may be used.

In fabrication procedures, the sizing material is first chemically joined to the polymeric fibers. The technique to accomplish this is normally selected from the group consisting of glow discharge induced reaction, ultraviolet induced reaction, free-radical induced reaction, and catalytic reaction. The preferred technique is glow discharge induced reaction.

In the preferred procedure, the properly sized polymeric fibers are introduced into a reaction vessel which is then evacuated to a level of from about 0.13 to 13 Pa to degas the fibers. A flowing stream of sizing agent is then introduced into the evacuated reaction vessel and maintained at a pressure of from about 1.3 to 133 Pa. Best results are obtained if the sizing agent pressure in the reaction vessel is maintained at a level of from about 7-35 Pa. Methylmethacrylate in the gaseous state is the preferred sizing agent.

During the sizing procedure, the fibers in the reaction vessel are suitably agitated, as by rotation or shaking of the vessel, to assure exposure of all fiber surfaces to the sizing agent. A high frequency electromagnetic field, such as is created by a microwave unit, is then applied to the contents of the vessel. It is preferred that the field have a frequency of up to about 100 MHz (more preferably from about 5-15 MHz) at a power level of at least about 20 W. This treatment of the fibers in the presence of the sizing agent causes glow discharge polymerization of the sizing agent on the surfaces of the fibers. The time of exposure is variable dependent upon the quantity of fibers being processed and the surface area and density thereof. In one exemplary case, 30 minutes of exposure time is appropriate, for a 0.05 kg quantity of fibers having a diameter of about 10 $\mu$m and a density of about 1 g./cm$^3$. Proper equivalent exposure times may be employed for other quantities and types of fibers. Sizing of the fibers with MMA using glow discharge polymerization causes the MMA molecules to become chemically joined to the surface molecules of the polymeric fibers.

Following sizing, the fibers may be mixed with matrix. Typically, the fibers are initially mixed with monomer, and the mixture subjected to polymerization. For example, where liquid methylmethacrylate is used as the monomer, polymerization may be accomplished using conventional addition polymerization techniques. For example, the MMA may be caused to polymerize by addition of a suitable amount of an initiator such as benzoyl peroxide. Polymerization of the MMA in the presence of the sized fibers causes the MMA during such polymerization to chemically join with the sizing on the fibers and thus produce a strong chemical coupling of the resultant polymethylmethacrylate to the acrylate sizing on the fibers.

Figure 2:
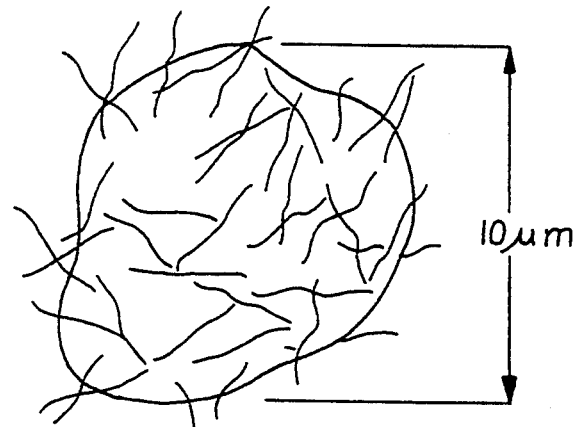
FIG. 2 is a greatly enlarged, schematic cross-sectional representation of a PMMA powder particle with reinforcing fibers within the particle and especially adapted for incorporation in a bone cement composition, with the way in which certain of the fibers protrude through the outer surface of the particle being illustrated.

The penultimate step in preparation of the particulate powder involves reducing the bulk reinforced polymer to the desired particle size. As indicated, the powder should have an average particle size of from about 5-100 $\mu$m. A proportion of very fine powder, less than 0.1 $\mu$m, is also desirable. The powdered material is produced by milling relatively large pieces of the sized fiber reinforced polymer. Mixing or grinding of the polymer has the advantage that some of the ends of the reinforcing fibers are exposed during fracturing of the bulk polymer as schematically depicted in FIG. 2. Reducing the temperature during milling to 0° C. or less facilitates brittle fracture of the bulk polymer and exposure of fiber ends.

The fiber reinforced powder made up of particles such as illustrated in FIG. 2 is next blended with an additional quantity of sized fibers which may constitute from about 1% to about 15% by weight of the mixture. If a radiopaque agent is used, it may also be combined with the powder and additional sized fibers. Best results are obtained if the radiopaque agent is also sized using glow discharge polymerization and a sizing agent of the same type as used for sizing the polymeric fibers. Thus, if MMA is used to size the fibers, MMA should also be used to size the radiopaque agent. Bulk polymer reduction and the addition of extra fiber serves to create final powder particles having reinforcing fibers extending through and at least partially out of the particles, as shown in FIG. 2. Fibers of this type are important in the production of bone cements, as will be described.

CONTINUOUS MEDIUM FOR BONE CEMENT

The same general principles described previously can also be employed in the fabrication of continuous media used in bone cements. Again, such media broadly include a polymeric matrix with sized fibers therein.

For purposes of continuous bone cement media, the same fibers described with reference to the particulate powder may be employed. However, the fiber content of such media will generally be lower than the fiber content of the powder, i.e., the media should contain from about 6-20 volume percent of sized fibers. Moreover, in this context the length of the fibers may be greater, with a length of up to about 5 mm having been found to be suitable.

Similarly, the polymeric matrix fraction of the continuous medium is the same as that used in connection with the powders, although there will be correspondingly a greater proportion of matrix present in the continuous media, as compared with the particulate powder product.

The sizing materials and sizing techniques described previously are also used in the creation of the continuous media products of the invention. If radiopaque agents are to be used in the continuous media, the same considerations, techniques and ingredients previously detailed, are used.

BONE CEMENT

A complete bone cement may be prepared by the mixture of a particulate powder (including fibers extending partially out of the particles) and continuous medium made in accordance with the invention. The final cement should contain from about 55-80% by weight powder, with the balance being continuous medium.

Generally speaking, the final bone cement and continuous medium are created simultaneously by the mixing of a precursor monomer to constitute the continuous medium, with the appropriate quantity of previously prepared powder. For example, the appropriate quantity of MMA monomer may be mixed with the particulate powder, with the MMA then being subjected to final polymerization. Where MMA is used, small amounts of additives may be used to promote room temperature polymerization. Exemplary additives are accelerators (e.g., N,N-dimethyl paratoluidine), initiators (e.g., benzoyl peroxide) and stabilizers (e.g., hydroquinone). Typically, the mixture and polymerization of precursor monomer and powder is done just prior to use of the cement for attachment of an orthopaedic implant.

During incorporation of the sized fiber-reinforced powder into the continuous medium, the liquid precursor monomeric material, the latter contacts the polymerized matrix of the particles, thereby solubilizing at least a part of the surfaces of the particles, so that there is intermixing of the precursor monomer undergoing polymerization to form the continuous medium, with the previously polymerized matrix. This intermixing contributes to the stability and strength of the bone cement, and increases the functional life thereof.

The proportion of fibers in the complete bone cement, and the ratio of particulate powder to continuous medium, influence the viscosity of the cement. Accordingly, these parameters may be adjusted within the ranges described so as to achieve the proper viscosity required for ease of use in a surgical context. In many cases, it is desirable to effect mixing of the cement components in a vacuum mixer, or to use other precautions to minimize bubble entrapment. The full strengthening effect of the sized reinforced fibers is best realized when the size and number of entrapped bubbles are reduced to a minimum.

The resulting bone cement thus comprises fiber-reinforced continuous medium of physiologically acceptable polymeric material, with particulate powder dispersed therein and made up of polymeric matrix and reinforcing fibers extending through and at least partially out of the particles. The polymeric material of the continuous medium is chemically joined with both the reinforcing fibers thereof and the fibers extending from the powder particles to create a cement of enhanced strength. Where radiopaque agents are employed in the particles and/or continuous medium, such would also of course be present in the final cement. Inasmuch as the previously described particulate powder and continuous media are used in the preparation of the final bone cement, the parameters discussed above pertaining to fibers, sizing agents and matrices apply to the finished bone cement as well.

COATING FOR ORTHOPAEDIC IMPLANT

The fundamental orthopaedic compositions of the invention can also be modified to obtain coatings adapted for direct application to an orthopaedic appliance or implant, such as a metallic or polymeric prosthetic hip implant. Broadly speaking, such coatings include a physiologically acceptable polymeric continuous phase with sized reinforcing fibers dispersed in the continuous phase. When such coatings are applied over the outer surfaces of an implant or appliance, the coatings are chemically joined with the surface, thereby maximizing the strength of the composite.

Insofar as the fiber component of such coatings is concerned, the parameters described above respecting the continuous medium for bone cements are fully applicable. Similarly, the continuous phase portion of the coatings are the same as those used in the continuous media for bone cements.

Following the fiber sizing operation, the fibers are mixed with precursor monomer, and most preferably liquid MMA for polymerization using conventional techniques, preferably addition polymerization. The MMA may be caused to polymerize through use of an initiator such as benzoyl peroxide. If desired, the implant may be provided with a roughened surface which enhances adherence of the coating thereto. Alternately, the sizing agent used in preparation of the coating reinforcement may be applied directly to the outer surface of the implant, using the techniques described previously. In this fashion, the sizing agent is chemically joined with the outer surface of the implant and the coating to be applied thereover.

The coatings may be applied to the implants well prior to actual use thereof. For example, the manufacturer of a metal or polymeric implant may coat its implant product at the time of fabrication, and the coated orthopaedic device may then be shelved until needed. Additionally, after such implant coating, the outer surface of the coating may be etched with MMA monomer or other suitable etchant, either in liquid or vapor form. From about 0.1 to 1 mm of the surface of the coating is desirably removed, to expose the ends of sized fibers, so that such fibers will extend across the interface between the implant coating and bone cement.

Orthopaedic Implant Installation System

The invention ultimately provides a greatly improved system for the permanent implantation of orthopaedic devices. Such a system includes the described coating on the surface of the orthopaedic device, together with bone cement serving to contact and adhere to a bone surface while also contacting the implant coating.

During orthopaedic surgery, involving, for example, a hip joint replacement where there has been a fracture of the upper end of the femur, the femoral head is removed by a saw or other equivalent device which produces a smooth cut, thus exposing the spongy bone and marrow cavity within the hard cortical bone. The marrow cavity is then reamed to remove spongy bone and marrow to an extent that the rigid, previously coated and etched implant may be inserted into the cavity along with an appropriate quantity of bone cement.

Figure 5:
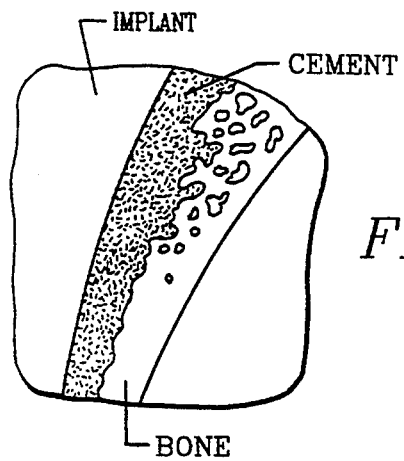
FIG. 5 is an enlarged, schematic, fragmentary cross-sectional representation of a rigid implant in a bone cavity and illustrating the way in which bone cement is used to firmly affix the implant to the interstices of the bone.

The preferred bone cement previously described made up of the continuous medium and particulate powder is then injected into the reamed bone cavity to fill the canal with bone cement. The rigid, precoated orthopaedic implant is then inserted into the cement-filled bone cavity. There is a firm chemical joinder of the coated implant to the bone structure not only because of the presence of the cement initially introduced into the bone cavity, but also by virtue of the fact that the cement has completely filled the interstices of the internal bone structure as is illustrated in FIG. 5. The reinforcing fibers in the bone cement are of sufficient flexibility that they do not impede free flow of the cement composition into the small interstices of the bone structure, or bridge openings leading to such interstices, as has occurred with prior fiber-reinforced orthopaedic cements.

Figure 4:
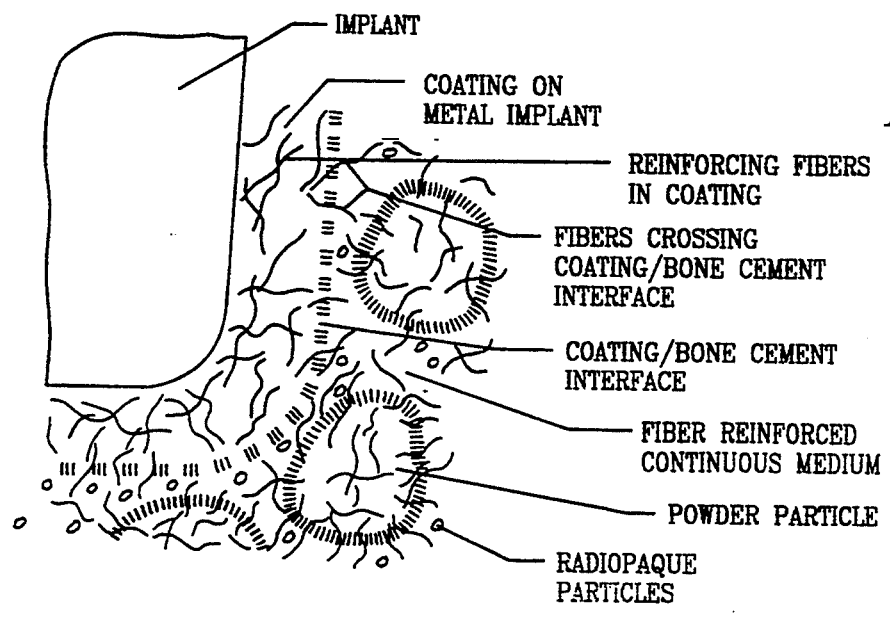
FIG. 4 is a greatly enlarged, schematic fragmentary cross-sectional view showing a rigid implant with a sized fiber reinforced PMMA coating thereover, and with the coated implant imbedded in a quantity of bone cement of the type depicted in FIG. 3, and further showing the interface between the implant coating and bone cement.

FIG. 4 illustrates an implant disposed within a bone cavity, and held therein by the system of the invention. As depicted, the sized fibers reinforcing both the continuous medium of the cement and the implant coating, as well as the fibers protruding from the particles, extend across the coating/bone cement interface to enhance the bonding and chemical joinder between the coating and cement.

ALTERNATIVE EMBODIMENTS

Figure 3:
FIG. 3 is a greatly enlarged, schematic cross-sectional representation of a reinforced bone cement containing the particulate powder of the invention dispersed in a continuous medium along with radiopaque particles.

For certain orthopaedic applications, it may not be necessary to incorporate sized fibers in the powder particles as previously described and specifically illustrated in FIG. 3 of the drawings. Since fatigue cracking occurs primarily in the continuous medium of the bone cement, reinforcement of this medium only realizes much of the potential benefit of the invention. In this manner, less changes in current bone cement manufacturing processes are required.

In carrying out this alternate embodiment of the invention, sized fibers and sized radiopaque powders are dry blended, but with unreinforced PMMA powder. The blend is then mixed with room temperature precursor MMA (liquid) monomer to yield a bone cement with the coupled radiopacifier and reinforcing fibers in the continuous medium only.

An alternative process for sizing of the fibers includes rotation of the reaction vessel to insure exposure of the fibers to the sizing agent throughout the sizing step. Similarly, the fibers may be agitated by a variety of means including, but not limited to, mechanical, electromagnetic or rheologic processes such as shaking, tumbling, or free fall in a column, electromagnetic levitation or electrostatic self-repulsion, and the creation of vortices in the flowing (gaseous) coupling agent.

Instead of milling or grinding the bulk reinforced polymer during powder preparation, the powder particles may be prepared by combining fiber incorporation with bead polymerization.

We claim:

1. An orthopaedic composition, comprising:
   an amount of a physiologically acceptable polymeric matrix material; and
   a quantity of fibers disbursed in said matrix for enhancing functional qualities of the composition, said fibers having a layer of a sizing material thereover which is chemically joined to the surface of the fibers, said sizing material on the fibers also being chemically joined with the matrix material,
   said fibers being present in said composition in an effective amount for reinforcing said matrix and having an average length of from about 1 $\mu$m to about 2 cm,
   said fibers having a stiffness defined as the product of the tensile elastic modulus of the fibers and the area moment of inertia of the fibers, said stiffness being from about $1.0 \times 10^{-13}$ to $150 \times 10^{-13}$ Nm$^2$.

2. An orthopaedic composition as set forth in claim 1, wherein said sizing material is directly chemically joined to said fibers.

3. An orthopaedic composition as set forth in claim 1, wherein said sizing material is a coupling agent different from said matrix.

4. An orthopaedic composition as set forth in claim 1, wherein said fibers comprise polymeric reinforcing fibers formed of a relatively high strength polymer of intermediate stiffness.

5. An orthopaedic composition as set forth in claim 1, said composition being in the form of a particulate powder adapted for placement in a continuous medium to form a bone cement.

6. An orthopaedic composition as set forth in claim 5, the particles of said powder having an average size of from about 5 to 100 $\mu$m.

7. An orthopaedic composition as set forth in claim 5, said fibers being in the form of polymeric fibers.

8. An orthopaedic composition as set forth in claim 7, said fibers being selected from the group consisting of polyaramids, polyesters, polyalkenes and polyamides.

9. An orthopaedic composition as set forth in claim 7, said fibers having a diameter of from about 1 $\mu$m to 100 $\mu$m.

10. An orthopaedic composition as set forth in claim 9, wherein at least certain of said fibers have a diameter of from about 2-15 $\mu$m.

11. An orthopaedic composition as set forth in claim 7, said fibers having a length of up to about the diameter of said particle.

12. An orthopaedic composition as set forth in claim 12, wherein said stiffness is from about $10 \times 10^{-13}$ to $75 \times 10^{-13}$ Nm$^2$.

13. An orthopaedic composition as set forth in claim 7, wherein said fibers have a room temperature fatigue strength of at least about 7 MPa at $10^6$ cycles.

14. An orthopaedic composition as set forth in claim 13, said fatigue strength being at least 30 MPa at $10^6$ cycles.

15. An orthopaedic composition as set forth in claim 7, said fibers being present in said powder at a level of from about 6 to 70 volume percent.

16. An orthopaedic composition as set forth in claim 15, said level being about 50 volume percent.

17. An orthopaedic composition as set forth in claim 5, wherein said matrix is a substituted or unsubstituted acrylate.

18. An orthopaedic composition as set forth in claim 17, said matrix being polymethylmethacrylate.

19. An orthopaedic composition as set forth in claim 18, said polymethylmethacrylate having a viscosity average molecular weight of not less than about $1 \times 10^5$ g./mole.

20. An orthopaedic composition as set forth in claim 5, wherein said sizing material is selected from the group consisting of ethyl silane, methylmethacrylate, ethylmethacrylate, ethylene, propylene and methane.

21. An orthopaedic composition as set forth in claim 20, wherein said sizing material is an acrylate.

22. An orthopaedic composition as set forth in claim 20, wherein said sizing material is methylmethacrylate.

23. An orthopaedic composition as set forth in claim 5, including a radiopaque agent, said agent having said sizing material thereover.

24. An orthopaedic composition as set forth in claim 5, wherein said sizing material has been chemically joined to the fibers by a technique selected from the group consisting of glow discharge induced reaction, ultraviolet induced reaction, free-radical induced reaction and catalytic reaction.

25. An orthopaedic composition as set forth in claim 24, wherein glow discharge reaction of the sizing material while in contact with said fibers is carried out at a frequency of up to about 100 MHz at a power level of at least about 20 W.

26. An orthopaedic composition as set forth in claim 25, wherein glow discharge reaction of the sizing material while in contact with said fibers is carried out at a frequency between about 5-15 MHz 27. An orthopaedic composition as set forth in claim 24, wherein glow discharge reaction of the sizing material while in contact with said fibers is carried out for a time period equivalent to 30 minutes exposure for each 0.05 kg of fibers having a density of about 1 g/cm$^3$ and an average diameter of about 10 $\mu$m.

28. An orthopaedic composition as set forth in claim 1, said composition being in the form of a continuous medium adapted for mixing with reinforced particles to form a bone cement.

29. An orthopaedic composition as set forth in claim 28, said fibers being in the form of polymeric fibers.

30. An orthopaedic composition as set forth in claim 29, said fibers being selected from the group consisting of polyaramids, polyesters, polyalkenes and polyamides.

31. An orthopaedic composition as set forth in claim 29, said fibers having a diameter of from about 1 $\mu$m to 100 $\mu$m.

32. An orthopaedic composition as set forth in claim 31, wherein at least certain of said fibers have a diameter of from about 2-15 $\mu$m.

33. An orthopaedic composition as set forth in claim 28, said fibers having a length of up to about 5 min.

34. An orthopaedic composition as set forth in claim 29, wherein said stiffness is from about $10 \times 10^{-3}$ to $75 \times 10^{-13}$ Nm$^2$.

35. An orthopaedic composition as set forth in claim 28, wherein said fibers have a room temperature fatigue strength of at least about 7 MPa at $10^6$ cycles.

36. An orthopaedic composition as set forth in claim 35, said fatigue strength being at least 30 MPa at $10^6$ cycles.

37. An orthopaedic composition as set forth in claim 28, said fibers being present in said medium at a level of from about 6-20 volume percent.

38. An orthopaedic composition as set forth in claim 38, wherein said matrix is a substituted or unsubstituted acrylate.

39. An orthopaedic composition as set forth in claim 38, said matrix being polymethylmethacrylate.

40. An orthopaedic composition as set forth in claim 39, said polymethylmethacrylate having a viscosity average molecular weight of not less than about $1 \times 10^5$ g./mole.

41. An orthopaedic composition as set forth in claim 28, wherein said sizing material is selected from the group consisting of ethyl silane, methylmethacrylate, ethylmethacrylate, ethylene, propylene and methane.

42. An orthopaedic composition as set forth in claim 41, wherein said sizing material is an acrylate.

43. An orthopaedic composition as set forth in claim 41, wherein said sizing material is polymethylmethacrylate.

44. An orthopaedic composition as set forth claim 28, including a radiopaque agent, said agent having said sizing material thereover.

45. An orthopaedic composition as set forth in claim 28, wherein said sizing material has been chemically joined to the fibers by a technique selected from the group consisting of glow discharge induced reaction, ultraviolet induced reaction, free-radical induced reaction and catalytic reaction.

46. An orthopaedic composition as set forth in claim 45, wherein glow discharge reaction of the sizing material while in contact with said fibers is carried out at a frequency of up to about 100 MHz at a power level of at least about 20 W.

47. An orthopaedic composition as set forth in claim 46, wherein glow discharge reaction of the sizing material while in contact with said fibers is carried out at a frequency between about 5-15 MHz.

48. An orthopaedic composition as set forth in claim 45, wherein glow discharge reaction of the sizing material while in contact with said fibers is carried out for a time period equivalent to 30 minutes exposure for each 0.05 kg of fibers having a density of about 1 g/cm$^3$ and an average diameter of about 10 μm.

49. An orthopaedic composition as set forth in claim 1, said composition being in the form of a coating for application to an orthopaedic appliance.

50. An orthopaedic composition as set forth in claim 49, said fibers being in the form of polymeric fibers.

51. An orthopaedic composition as set forth in claim 50, said fibers being selected from the group consisting of polyaramids, polyesters, polyalkenes and polyamides.

52. An orthopaedic composition as set forth in claim 50, said fibers having a diameter of from about 1μm to 100μm.

53. An orthopaedic composition as set forth in claim 52, wherein at least certain of said fibers have a diameter of from about 2-15 μm.

54. An orthopaedic composition as set forth in claim 49, wherein said stiffness is from about $10 \times 10^{-13}$ to $75 \times 10^{-13}$ Nm$^2$.

55. An orthopaedic composition as set forth in claim 49, wherein said fibers have a room temperature fatigue strength of at least about 7 MPa at $10^6$ cycles.

56. An orthopaedic composition as set forth in claim 55, said fatigue strength being at least 30 MPa at $10^6$ cycles.

57. An orthopaedic composition as set forth in claim 49, said fibers being present at a level of from about 6 to 70 volume percent.

58. An orthopaedic composition as set forth in claim 57, said level being about 50 volume percent.

59. An orthopaedic composition as set forth in claim 49, wherein said matrix is a substituted or unsubstituted acrylate.

60. An orthopaedic composition as set forth in claim 59, said matrix being polymethylmethacrylate.

61. An orthopaedic composition as set forth in claim 60, said polymethylmethacrylate having a viscosity average molecular weight of not less than about $1 \times 10^5$ g./mole.

62. An orthopaedic composition as set forth in claim 49, wherein said sizing material is selected from the group consisting of ethyl silane, methylmethacrylate, ethylmethacrylate, ethylene, propylene and methane.

63. An orthopaedic composition as set forth in claim 62, wherein said sizing material is an acrylate.

64. An orthopaedic composition as set forth in claim 63, wherein said sizing material is polymethylmethacrylate.

65. An orthopaedic composition as set forth in claim 49, including a radiopaque agent, said agent having said sizing material thereover.

66. An orthopaedic composition as set forth in claim 49, wherein said sizing material has been chemically joined to the fibers by a technique selected from the group consisting of glow discharge induced reaction, ultraviolet induced reaction, free-radical induced reaction and catalytic reaction.

67. An orthopaedic composition as set forth in claim 66, wherein glow discharge reaction of the sizing material while in contact with said fibers is carried out at a frequency of up to about 100 MHz at a power level of at least about 20 W.

68. An orthopaedic composition as set forth in claim 67, wherein glow discharge reaction of the sizing material while in contact with said fibers is carried out at a frequency between about 5-15 MHz.

69. An orthopaedic composition as set forth in claim 67, wherein glow discharge reaction of the sizing material while in contact with said fibers is carried out for a time period equivalent to 30 minutes exposure for each 0.05 kg of fibers having a density of about 1 g/cm$^3$ and an average diameter of about 10 μm.

70. A bone cement comprising:
a continuous medium comprising a physiologically acceptable polymeric material; and
a particulate powder dispersed in said continuous medium, the particles making up said powder including a physiologically acceptable polymeric matrix and reinforcing fibers extending through and at least partially out of the particles, said polymeric material of the continuous medium being chemically joined with said fibers.

71. The bone cement of claim 70, said powder comprising from about 55-80% by weight of the bone cement.

72. The bone cement of claim 70, said continuous medium comprising a substituted or unsubstituted acrylate.

73. The bone cement of claim 72, said continuous medium comprising polymethylmethacrylate.

74. The bone cement of claim 70, said continuous medium including therein fibers distinct from the fibers present in said particles.

75. The bone cement of claim 70, said continuous medium including therein an amount of sized radiopaque agent.

76. The bone cement of claim 70, said fibers being selected from the group consisting of polyaramids, polyesters, polyalkenes and polyamides.

77. The bone cement of claim 77, said fibers having a layer of sizing material thereover chemically joined to the surface thereof, said sizing material on the fibers also being chemically joined with said matrix material.

78. The bone cement of claim 77, said continuous medium also being chemically joined to the sizing material on said fibers.

79. A method of preparing an orthopaedic composition comprising the steps of:
chemically bonding a layer of a sizing material onto the outer surfaces of a quantity of fibers; and
polymerizing a monomeric material in the presence of said sized fibers for chemically joining the sized fibers to the resultant polymerized material in order to enhance the properties of the orthopaedic composition.

80. A method of preparing an orthopaedic composition as set forth in claim 79, wherein said step of chemically bonding a sizing material to the fibers comprises using a technique selected from the group consisting of glow discharge induced reaction, ultraviolet induced reaction, free-radical induced reaction, and catalytic reaction.

81. A method of preparing an orthopaedic composition as set forth in claim 80, wherein glow discharge polymerization is employed to couple a sizing layer onto the surface of the fibers, said glow discharge polymerization being effected by exposing the surfaces of the fibers and the sizing material to an electromagnetic field at a frequency of 1 to 100 MHz at a power of at least 20 W per square centimeter of fiber surface area.

82. A method of preparing an orthopaedic composition as set forth in claim 81, wherein said composition is in the form of a bulk solid, and further including the steps of comminuting said bulk solid to form a particulate powder.

83. An orthopaedic composition, consisting essentially of:
an amount of a physiologically acceptable polymeric matrix material, said material selected from the group consisting of substituted acrylates and unsubstituted acrylates; and
a quantity of fibers disbursed in said matrix for enhancing functional qualities of the composition, said fibers having a layer of a sizing material thereover which is chemically joined to the surface of the fibers, said sizing material of the fibers also being chemically joined with the matrix material,
said fibers being present in said composition in an effective amount for reinforcing said matrix and having an average length of from about 1 $\mu$m to about 2 cm,
said fibers having a stiffness defined as the product of the tensile elastic modulus of the fibers and the area moment of inertia of the fibers, said stiffness being from about $1.0 \times 10^{-13}$ to $150 \times 10^{-13}$ Nm$^2$.

* * * * *

UNITED STATES PATENT AND TRADEMARK OFFICE
CERTIFICATE OF CORRECTION

PATENT NO. : 5,336,699
DATED : August 9, 1994
INVENTOR(S) : Cook, et. al.

It is certified that error appears in the above-indentified patent and that said Letters Patent is hereby corrected as shown below:

Title page, item [73], Assignee:  Add Curators of University of Missouri, Columbia, MO--.

Signed and Sealed this

Twentieth Day of June, 1995

Attest:

BRUCE LEHMAN

*Attesting Officer*    *Commissioner of Patents and Trademarks*